(12) United States Patent  
Zucherman et al.

(10) Patent No.: US 6,695,842 B2
(45) Date of Patent: Feb. 24, 2004

(54) INTERSPINOUS PROCESS DISTRACTION SYSTEM AND METHOD WITH POSITIONABLE WING AND METHOD

(75) Inventors: James F. Zucherman, San Francisco, CA (US); Ken Y. Hsu, San Francisco, CA (US); Charles J. Winslow, Walnut Creek, CA (US); Henry A. Klyce, Piedmont, CA (US); John Flynn, Concord, CA (US)

(73) Assignee: St. Francis Medical Technologies, Inc., Concord, CA (US)

( * ) Notice: Subject to any disclaimer, the term of this patent is extended or adjusted under 35 U.S.C. 154(b) by 163 days.

(21) Appl. No.: 10/014,118

(22) Filed: Oct. 26, 2001

(65) Prior Publication Data

US 2002/0091446 A1 Jul. 11, 2002

Related U.S. Application Data

(63) Continuation-in-part of application No. 09/799,215, filed on Mar. 5, 2001, which is a continuation-in-part of application No. 09/473,173, filed on Dec. 28, 1999, now Pat. No. 6,235,030, which is a continuation of application No. 09/179,570, filed on Oct. 27, 1998, now Pat. No. 6,048,342, which is a continuation-in-part of application No. 09/474,037, filed on Dec. 28, 1999, now Pat. No. 6,190,387, which is a continuation of application No. 09/175,645, filed on Oct. 20, 1998, now Pat. No. 6,068,630, which is a continuation-in-part of application No. 09/200,266, filed on Nov. 25, 1998, now Pat. No. 6,183,471, which is a continuation of application No. 09/139,333, filed on Aug. 25, 1998, now Pat. No. 5,876,404, which is a continuation of application No. 08/958,281, filed on Oct. 27, 1997, now Pat. No. 5,860,977.

(60) Provisional application No. 60/306,263, filed on Jul. 18, 2001.

(51) Int. Cl.⁷ .............................................. A61B 17/70

(52) U.S. Cl. ...................... 606/61; 623/17.11

(58) Field of Search ............... 606/60, 61; 623/17.11, 623/17.15, 17.16

(56) References Cited

U.S. PATENT DOCUMENTS

| 2,677,369 A | 5/1954 | Knowles |
| 3,426,364 A | 2/1969 | Lumb |
| 3,648,691 A | 3/1972 | Lumb et al. |
| 3,867,728 A | 2/1975 | Stubstad et al. |

(List continued on next page.)

FOREIGN PATENT DOCUMENTS

| CA | 2015507 | 1/1991 |
| DE | 2821678 A1 | 4/1980 |
| DE | 3113142 A1 | 1/1982 |
| EP | 140790 A2 | 10/1984 |
| EP | 146347 A1 | 12/1984 |
| EP | 322334 A1 | 12/1988 |
| EP | 0677277 A2 | 10/1995 |
| EP | 0767636 B1 | 4/1997 |

(List continued on next page.)

OTHER PUBLICATIONS

Minns, R.J., et al., *Preliminary Design and Experimental Studies of a Novel Soft Implant for Correcting Sagittal Plane Instability in the Lumbar Spine*, SPINE vol. 22, No. 16, pp. 1819–1825, © 1997, Lippincott–Raven Publishers.

Waldemar Link, brochure entitled *Wirbelsäulen–Chirurgie: Instrumentarium Und Implantate Zur Wirbelsäulen–Chirurgie* (Spinal Surgery: Instrumentation and Implants for Spinal Surgery), Waldermar Link, Hamburg, Germany.

(List continued on next page.)

*Primary Examiner*—David O. Reip
(74) *Attorney, Agent, or Firm*—Fliesler Dubb Meyer & Lovejoy LLP (57) ABSTRACT

An implant that is implanted between adjacent spinous processes for the relief of pain associated with the spine. The device has a spacer to distract apart the adjacent spinous processes. To minimize trauma to the patient, the device has a tapered tissue expander to distract a previously created opening between the adjacent spinous processes. The device also has two wings. The position of one wing is adjustable to allow for ease of assembly in a patent.

57 Claims, 7 Drawing Sheets

U.S. PATENT DOCUMENTS

| | | |
|---|---|---|
| 3,875,595 A | 4/1975 | Froning |
| 4,309,777 A | 1/1982 | Patil |
| 4,349,921 A | 9/1982 | Kuntz |
| 4,369,769 A | 1/1983 | Edwards |
| 4,401,112 A | 8/1983 | Rezaian |
| 4,479,491 A | 10/1984 | Martin |
| 4,501,269 A | 2/1985 | Bagby |
| 4,553,273 A | 11/1985 | Wu |
| 4,554,914 A | 11/1985 | Kapp et al. |
| 4,599,084 A | 7/1986 | Nashef |
| 4,599,086 A | 7/1986 | Doty |
| 4,604,995 A | 8/1986 | Stephens et al. |
| 4,611,582 A | 9/1986 | Duff |
| 4,636,217 A | 1/1987 | Ogilvie et al. |
| 4,643,178 A | 2/1987 | Nastari et al. |
| 4,657,550 A | 4/1987 | Daher |
| 4,685,447 A | 8/1987 | Iversen et al. |
| 4,696,290 A | 9/1987 | Steffee |
| 4,714,469 A | 12/1987 | Kenna |
| 4,743,256 A | 5/1988 | Brantigan |
| 4,772,287 A | 9/1988 | Ray et al. |
| 4,790,303 A | 12/1988 | Steffee |
| 4,834,757 A | 5/1989 | Brantigan |
| 4,878,915 A | 11/1989 | Brantigan |
| 4,904,260 A | 2/1990 | Ray et al. |
| 4,904,261 A | 2/1990 | Dove et al. |
| 4,913,134 A | 4/1990 | Luque |
| 4,932,975 A | 6/1990 | Main et al. |
| 4,936,848 A | 6/1990 | Bagby |
| 4,946,378 A | 8/1990 | Hirayama et al. |
| 4,961,740 A | 10/1990 | Ray et al. |
| 4,969,888 A | 11/1990 | Scholten et al. |
| 5,011,484 A | 4/1991 | Breard |
| 5,015,247 A | 5/1991 | Michelson |
| 5,026,373 A | 6/1991 | Ray et al. |
| 5,035,716 A | 7/1991 | Downey |
| 5,047,055 A | 9/1991 | Bao et al. |
| 5,055,104 A | 10/1991 | Ray |
| 5,059,193 A | 10/1991 | Kuslich |
| 5,059,194 A | 10/1991 | Michelson |
| 5,084,049 A | 1/1992 | Asher et al. |
| 5,092,866 A | 3/1992 | Breard et al. |
| 5,123,926 A | 6/1992 | Pisharodi |
| 5,167,662 A | 12/1992 | Hayes et al. |
| 5,180,381 A | 1/1993 | Aust et al. |
| 5,192,327 A | 3/1993 | Brantigan |
| 5,258,031 A | 11/1993 | Salib et al. |
| 5,263,953 A | 11/1993 | Bagby |
| 5,290,312 A | 3/1994 | Kojimoto et al. |
| 5,304,178 A | 4/1994 | Stahurski |
| 5,306,309 A | 4/1994 | Wagner et al. |
| 5,352,225 A | 10/1994 | Yuan et al. |
| 5,387,213 A | 2/1995 | Breard et al. |
| 5,390,683 A | 2/1995 | Pisharodi |
| 5,395,372 A | 3/1995 | Holt et al. |
| 5,415,661 A | 5/1995 | Holmes |
| 5,443,514 A | 8/1995 | Steffee |
| 5,458,638 A | 10/1995 | Kuslich et al. |
| 5,458,641 A | 10/1995 | Ramirez Jimenez |
| 5,458,643 A | 10/1995 | Oka et al. |
| 5,470,333 A | 11/1995 | Ray |
| 5,496,318 A | 3/1996 | Howland et al. |
| 5,505,732 A | 4/1996 | Michelson |
| 5,514,180 A | 5/1996 | Heggeness et al. |
| 5,534,028 A | 7/1996 | Bao et al. |
| 5,534,029 A | 7/1996 | Shima |
| 5,540,689 A | 7/1996 | Sanders et al. |
| 5,549,679 A | 8/1996 | Kuslich |
| 5,562,736 A | 10/1996 | Ray et al. |
| 5,593,409 A | 1/1997 | Michelson |
| 5,609,634 A | 3/1997 | Voydeville |
| 5,645,597 A | 7/1997 | Krapiva |
| 5,645,599 A | 7/1997 | Samani |
| 5,653,761 A | 8/1997 | Pisharodi |
| 5,674,295 A | 10/1997 | Ray et al. |
| 5,674,296 A | 10/1997 | Bryan et al. |
| 5,676,702 A | 10/1997 | Ratron |
| 5,702,455 A | 12/1997 | Saggar |
| 5,725,582 A | 3/1998 | Bevan et al. |
| 5,766,252 A | 6/1998 | Henry et al. |
| 5,824,098 A | 10/1998 | Stein |
| 5,865,846 A | 2/1999 | Bryan et al. |
| 5,885,299 A | 3/1999 | Winslow et al. |
| 5,888,224 A | 3/1999 | Beckers et al. |
| 5,888,226 A | 3/1999 | Rogozinski |
| 5,976,186 A | 11/1999 | Bao et al. |
| 6,001,130 A | 12/1999 | Bryan et al. |
| 6,022,376 A | 2/2000 | Assell et al. |
| 6,113,639 A | 9/2000 | Ray et al. |
| 6,156,067 A | 12/2000 | Bryan et al. |
| 6,234,705 B1 | 5/2001 | Troxel |

FOREIGN PATENT DOCUMENTS

| | | |
|---|---|---|
| EP | 1138268 | 4/2001 |
| FR | WO 90/00037 | 1/1990 |
| FR | 2681525 A1 | 3/1993 |
| FR | 2707864 A1 | 1/1995 |
| FR | 2717675 | 9/1995 |
| FR | 2722980 A1 | 2/1996 |
| FR | 2780269 A1 | 12/1999 |
| FR | 2782911 A1 | 3/2000 |
| FR | 2806614 | 3/2000 |
| FR | 2806616 | 9/2001 |
| SU | 1484348 A1 | 6/1989 |
| WO | WO 91/16018 | 10/1991 |
| WO | WO 94/21185 | 9/1994 |
| WO | WO 94/26192 | 11/1994 |
| WO | WO 98/48717 | 11/1998 |
| WO | WO 99/26562 | 6/1999 |
| WO | WO 99/40866 | 8/1999 |
| WO | WO 99/42051 | 8/1999 |
| WO | WO 99/59669 | 11/1999 |
| WO | WO 00/04851 | 2/2000 |
| WO | WO 00/13619 | 3/2000 |
| WO | WO 00/13620 | 3/2000 |
| WO | WO 01/28442 A1 | 4/2001 |

OTHER PUBLICATIONS

Haruo Tsuji, et al., *Ceramic Interspinous Block (CISB)Assisted Anterior Interbody Fusion*, Journal of Spinal Disorders, vol. 3, No. 1, pp. 77–86, © 1990 Raven Press, Ltd., New York.

Richard W. Porter, MD, FRCS, FRCSE, *Spinal Stenosis and Neurogenic Claudication*, SPINE vol. 21, No. 17, pp. 2046–2052, © 1996, Lippincott–Raven Publishers.

INTERSPINOUS PROCESS DISTRACTION SYSTEM AND METHOD WITH POSITIONABLE WING AND METHOD

CROSS REFERENCE TO RELATED APPLICATION

This application claims priority to United States Provisional Patent Application entitled INTERSPINOUS PROCESS DISTRACTION SYSTEM AND METHOD WITH POSITIONABLE WING AND METHOD, filed Jul. 18, 2001, Serial No. 60/306,263 and is a continuation-in-part of U.S. patent application Ser. No. 09/799,215 filed Mar. 5, 2001, which is a continuation-in-part of U.S. patent application Ser. No. 09/473,173, filed Dec. 28, 1999. now U.S. Pat. No. 6,235,030, which is a continuation of U.S. patent application Ser. No. 09/179,570, filed Oct. 27, 1998, now U.S. Pat. No. 6,048,342, which is a continuation-in-part of U.S. patent application Ser. No. 09/474,037, Dec. 28, 1999, now U.S. Pat. No. 6,190,387, which is a continuation of U.S. patent application Ser. No. 09/175,645, filed Oct. 20, 1998, now U.S. Pat. No. 6,068,630, which is a continuation-in-part of U.S. patent application Ser. No. 09/200,266, filed Nov. 25, 1998, now U.S. Pat. No. 6,183,471, which is a continuation of U.S. patent application Ser. No. 09/139,333, filed Aug. 25, 1998, now U.S. Pat. No. 5,876,404, which is a continuation of U.S. patent application Ser. No. 08/958,281, filed Oct. 27, 1997, now U.S. Pat. No. 5,860,977. All of the above applications and patents are incorporated herein by reference.

FIELD OF THE INVENTION

The present invention is directed to an interspinous process implant system and method which can, for example, distract apart and maintain said distraction of adjacent spinous process.

BACKGROUND OF THE INVENTION

As the present society ages, it is anticipated that there will be an increase in adverse spinal conditions which are characteristic of older people. By way of example only, with aging comes increases in spinal stenosis (including, but not limited to, central canal and lateral stenosis), the thickening of the bones which make up the spinal column and facet arthropathy. Spinal stenosis is characterized by a reduction in the available space for the passage of blood vessels and nerves. Pain associated with such stenosis can be relieved by medication and/or surgery. Of course, it is desirable to eliminate the need for major surgery for all individuals and in particular for the elderly.

Accordingly, there needs to be developed procedures and implants for alleviating these and other spinal conditions, which procedures and implants are minimally invasive, can be tolerated by the elderly and can be performed preferably on an outpatient basis.

SUMMARY OF THE INVENTION

The present invention is directed to providing a minimally invasive apparatus and method for alleviating discomfort associated with the spinal column.

The present invention provides for apparatus and method for relieving pain by relieving the pressure and restrictions on the aforementioned blood vessels and nerves. Such alleviation of pressure is accomplished in the present invention through the use of an implant and method which distract the spinous process of adjacent vertebra in order to alleviate the problems caused by spinal stenosis and facet arthropathy and the like as well as other spinal ailments. While the implant and method particularly address the needs of the elderly, the invention can be used with individuals of all ages and sizes where distraction of the spinous process would be beneficial.

In one aspect of the invention, an implant is provided for relieving pain comprising a device positioned between a first spinous process and a second spinous process. The device includes a spinal column extension stop and a spinal column flexion non-inhibitor.

In a further aspect of the invention, the implant includes a first unit having a body with a guide or tissue expander and a first wing, with the first wing located at first end of the body. The guide extends from a second end of the body located distally from the first wing. The implant further includes a sleeve or spacer provided over said body. The implant further includes a second wing and a device for securing the second wing to the first unit, wherein the sleeve or spacer is located between the first and second wings.

In yet still a further aspect of the invention, the implant includes a sleeve which is rotatable relative to the wings of the implant in order to be able to accommodate the anatomical structure of spinous processes.

In still another aspect of the invention, the implant includes a second wing that is movable toward the first wing after the second wing is assembled to the first unit in the patient. In this aspect a fastener can be operated to cause the second wing to move toward the first wing. Accordingly, the implant can be easily assembled in the patient without concern for the shape of the spinous processes and then the first and second wings can be drawn together so that these wings are positioned closer to the spinous processes.

In another aspect the second wing includes an alignment tab which is received in an alignment groove of the first unit in order to guide the second wing as it is urged toward the first wing.

In another aspect of the invention a ramp mechanism is used to urge the second wing toward the first wing.

Other implants and methods within the spirit and scope of the invention can be used to release pain associated with the spine and/or increase the volume of the spinal canal thereby alleviating restrictions on vessels and nerves associated therewith and associated pain.

DETAILED DESCRIPTION OF THE INVENTION

Figure 1:
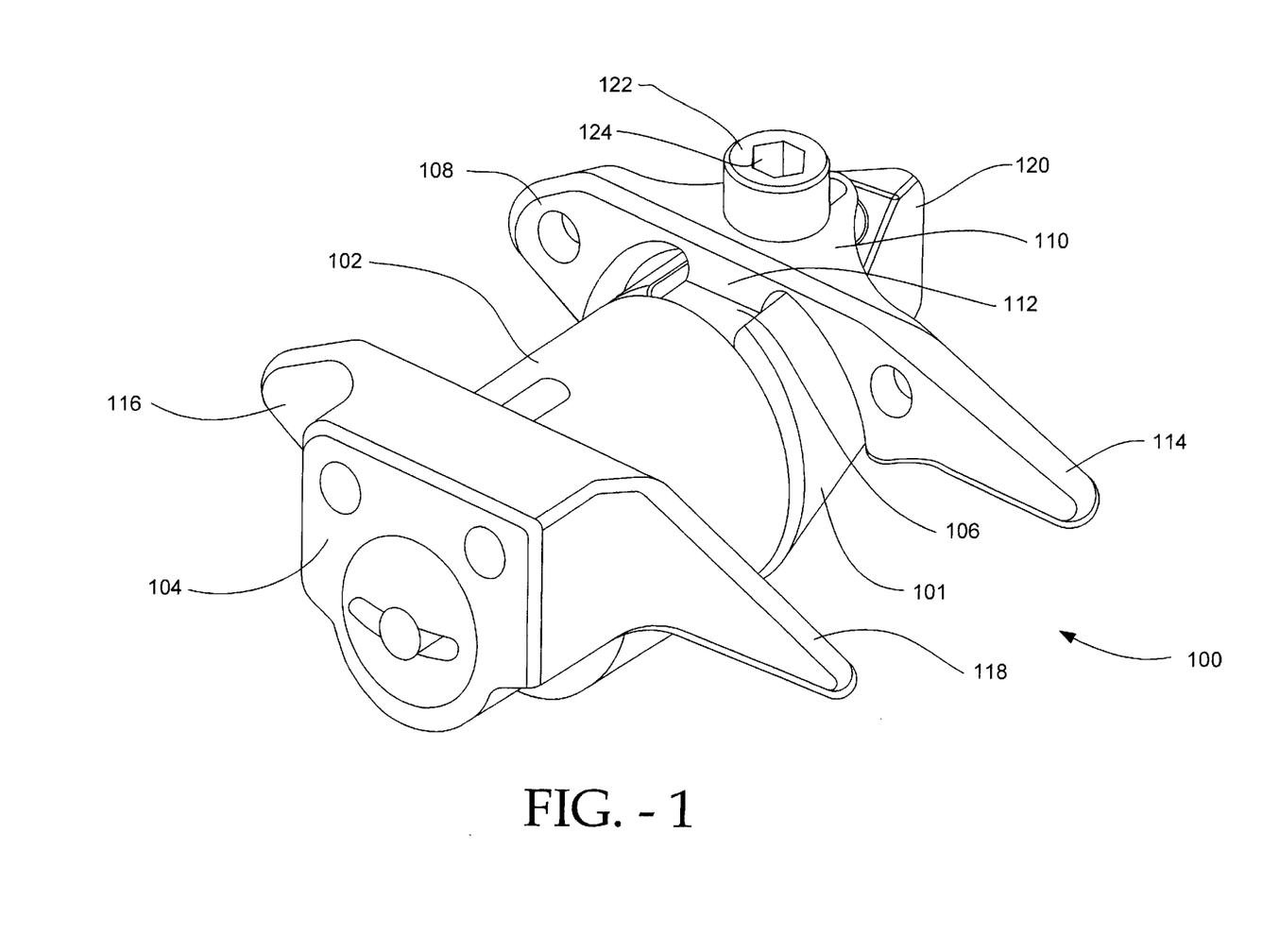
FIG. 1 is a perspective view of an embodiment of the present invention.

Referring to FIG. 1, the implant device 100 has a main body 101. The main body 101 includes a spacer 102, a first wing 104, a tapered front end, lead-in guide or tissue expander 120 and an alignment track 106. The main body 101 is inserted between adjacent spinous processes. Preferably, the main body 101 remains safely and permanently in place without attachment to the bone or ligaments. All of the components of the implant device 100 are made of biologically acceptable material such as, but are not limited to, high strength titanium alloy or stainless steel. Preferably the first wing 104 is laser welded to the main body 101.

The tip of the tissue expander 120 has the smallest diameter, allowing the tip to be inserted into a small initial dilated opening. The diameter and/or cross-sectional areas of the tissue expander 120 then gradually increases until it is substantially similar to the diameter of the main body 101 and spacer 102. The tapered front end 120 makes it easier for a physician to urge the implant device 100 between adjacent spinous processes. When urging the main body 101 between adjacent spinous processes, the front end 120 distracts the adjacent spinous processes to the diameter of the spacer 102. As shown in FIG. 1, the tissue expander 120 is a pyramid shape. In another embodiment the tissue expander preferably has an angle of twenty-five degrees that allows it to clear the facet. This reduces the length of the front end 120. One will appreciate that the shape of the tissue expander 120 can be other shapes such as, but not limited to, cone shaped, or any other shape with a small lead-in cross-section expanding into a larger cross-section. These types of shapes gradually distract the spinous processes to a sufficient distance so that the spacer 102 can conveniently fit between the spinous processes.

The spacer 102 can be made of stainless steel, titanium, a super-elastic material or silicone or other biologically acceptable material. The material can be rigid or resilient as desired. As shown in FIG. 1, the spacer 102 is an elliptically shaped cylinder. One will appreciate that the spacer can consist of other shapes such as, but not limited to, egg-shaped, round-shaped or saddle-shaped. For example, the spacer 102 can be saddle-shaped along the surface which engages the spinous processes so that the high edges and the lower central portions can more fully accommodate the shape of the spinous processes. Preferably, the spacer 102 can swivel, allowing the spacer 102 to self-align relative to the uneven surface of the spinous process. This ensures that compressive loads are distributed equally on the surface of the bone. By way of example only, the spacer 102 can have diameters of six millimeters, eight millimeters, ten millimeters, twelve millimeters and fourteen millimeters. These diameters refer to the height by which the spacer distracts and maintains apart the spinous process. Thus for an elliptical spacer the above selected height would represent the small diameter measurement from the center of the ellipse. The largest diameter would be transverse to the alignment, of the spinous process, one above the other. Smaller and larger diameters are within the scope of the invention.

The shape of the spacer 102 and for that matter the shape of the entire implant is such that for purposes of insertion between the spinous processes, the spinous processes do not need to be altered or cut away in any manner in order to accommodate the implant 100. Additionally, the associated ligaments do not need to be cut away and there would be very little or no damage to the other adjacent or surrounding tissues other than piercing through and separating, or dilating an opening in a ligament.

The first wing 104 has a lower portion 116 and an upper portion 118. The upper portion 118 is designed to preferably accommodate, in this particular embodiment, the anatomical form or contour of the L4 (for an L4-L5 placement) or L5 (for an L5-S1 placement) vertebra. It is to be understood that the same shape or variations of this shape can be used to accommodate other vertebra. The lower portion 116 is also rounded to accommodate, in a preferred embodiment, the vertebra. The lower portion 116 and upper portion 118 of the first wing 104 will act as a stop mechanism when the implant device 100 is inserted between adjacent spinous processes. The implant device 100 cannot be inserted beyond the surfaces of the first wing 104. Additionally, once the implant device 100 is inserted, the first wing 104 can prevent side-to-side, or posterior to anterior movement of the implant device 100.

The implant device 100 also has an adjustable wing 110. The adjustable wing 110 has a lower portion 108 and an upper portion 114. Similar to the first wing 104, the adjustable wing 110 is designed to accommodate the anatomical form or contour of the vertebra.

The adjustable wing 110 is secured to the main body 101 with a fastener 122 provided through tapered cavity 130. The adjustable wing 110 also has an alignment tab 112. When the adjustable wing 110 is initially placed on the main body 101, the alignment tab 112 engages the alignment track 106. The alignment tab 112 slides within the alignment track 106 and helps to maintain the adjustable wing 110 substantially parallel with the first wing 104 in this preferred embodiment. When the main body 101 is inserted into the patient and the adjustable wing 110 has been attached, the adjustable wing 110 also can prevent side-to-side, or posterior to anterior movement.

Figure 2:
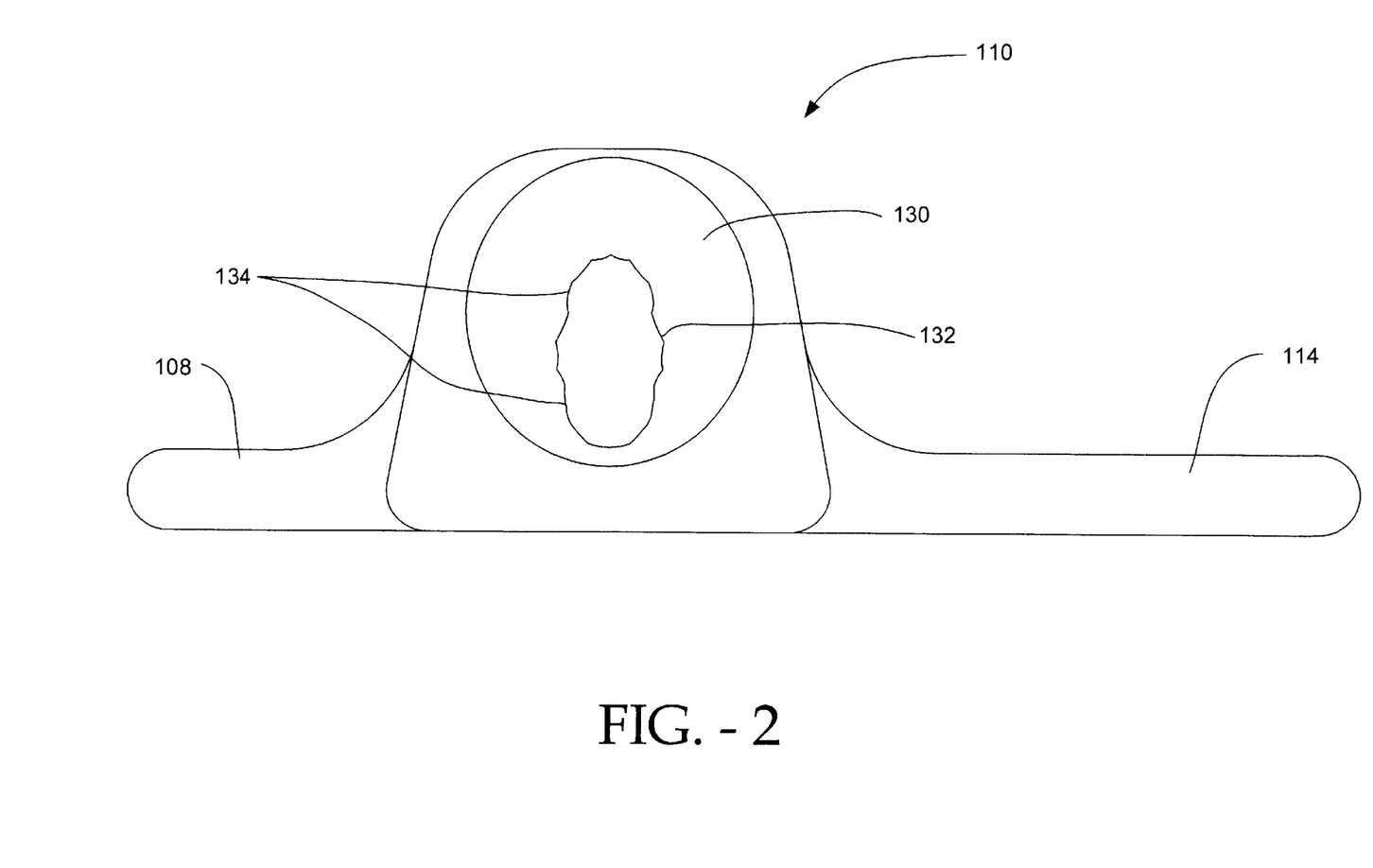
FIG. 2 is a top view of an embodiment of the adjustable wing of the present invention.

Referring now to FIG. 2, the adjustable wing 110 includes the above mentioned tapered cavity 130. The tapered cavity 130 has a middle portion 132, two end portions 134 and a tapered wall 131. The diameter of the middle portion 132 is larger than the diameter of either end portion 134. The tapered wall 131 has a larger diameter at the top surface of the adjustable wing 110 than at the bottom surface. Accordingly a cone-like shape is formed. When the fastener 122 engages the main body 101 and is rotated, the fastener 122 travels into the main body 101 (see FIG. 1). As the fastener 122 travels into the main body 101, the adjustable wing 110 will travel along the alignment track 106 towards the first wing 104. The alignment tab 112 engages the alignment track 106 and functions as a guide, keeping the adjustable wing 110 and the first wing 104 substantially parallel to each other.

Figure 3:
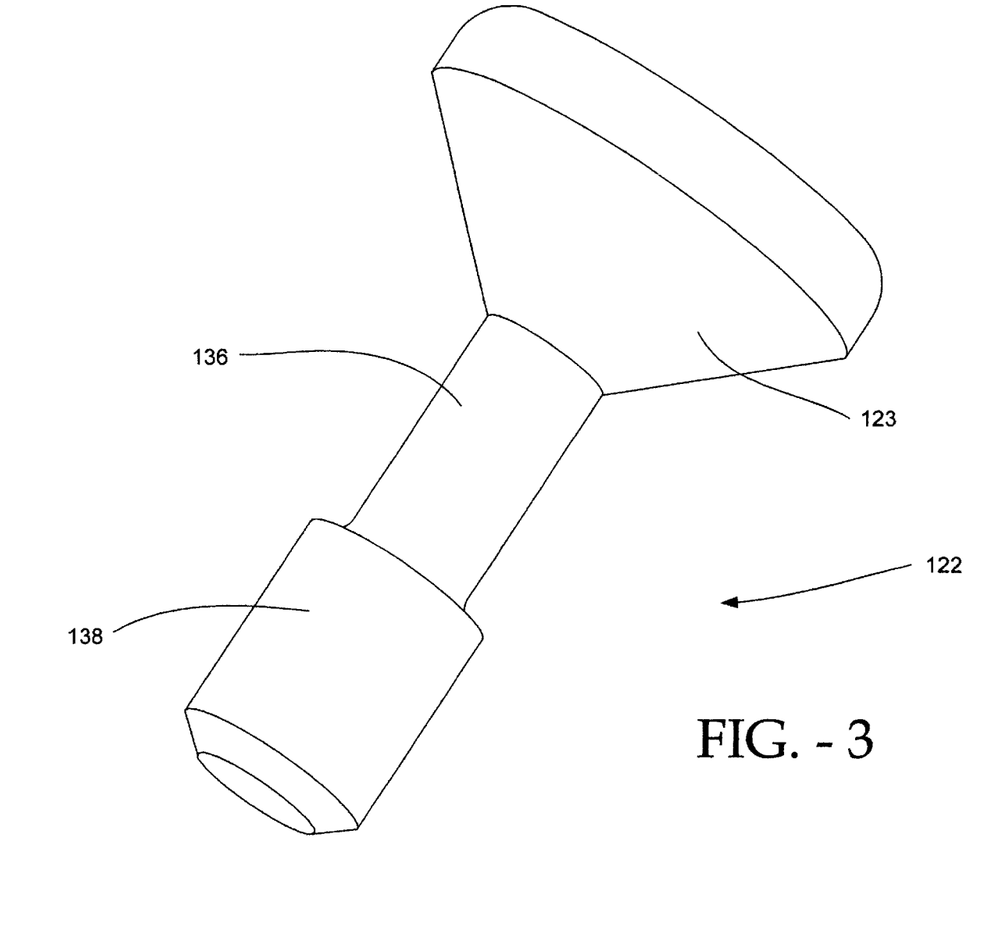
FIG. 3 is a perspective view of an embodiment of the fastener used in the present invention.

The fastener 122 has a tapered head 123, a middle section 136 and threaded bottom section 138 (see FIG. 3). The top end of the tapered head 123 was a diameter substantially similar to the diameter of the top surface of the tapered cavity 130. The diameter of the tapered head 123 is reduced as the tapered head meets the middle section 136. The slope of the tapered head 123 is similar to the slope of the tapered cavity 130 of the adjustable wing 110. The middle section 136 has a diameter substantially similar to the end portions 134 of the adjustable wing 110. The threaded bottom section 138 has a slightly larger diameter than the middle section 136 and is in one embodiment slightly smaller than the diameter of the middle portion 132 of the adjustable wing 110.

As the diameter of the end portions 134 are smaller than the diameter of the bottom section 138, the fastener 122 cannot initially be placed through the end portions 134 of the adjustable wing 110. Accordingly, to fasten the adjustable wing 110 to the main body 101, the threaded bottom section 138 of the fastener 122 is placed through the middle portion 132 of the adjustable wing 110 and into the main body 101. With a turn of the fastener 122, the threaded portion of the bottom section 138 will engage the main body 101.

In another preferred embodiment the diameter of threaded bottom section 138 is larger than the diameter of the middle portion of the adjustable wing 110. For this embodiment, the fasteners 122 is inserted into the cavity 130 by slicing the cavity 130 (FIG. 2) through the thinnest portion of the wall, spreading the wall open, inserting the middle section 136 in the cavity with the threaded bottom section 138 projection below the cavity 130, and laser welding the wall closed. The slicing step preferably includes using a carbide slicing device.

Figure 4:
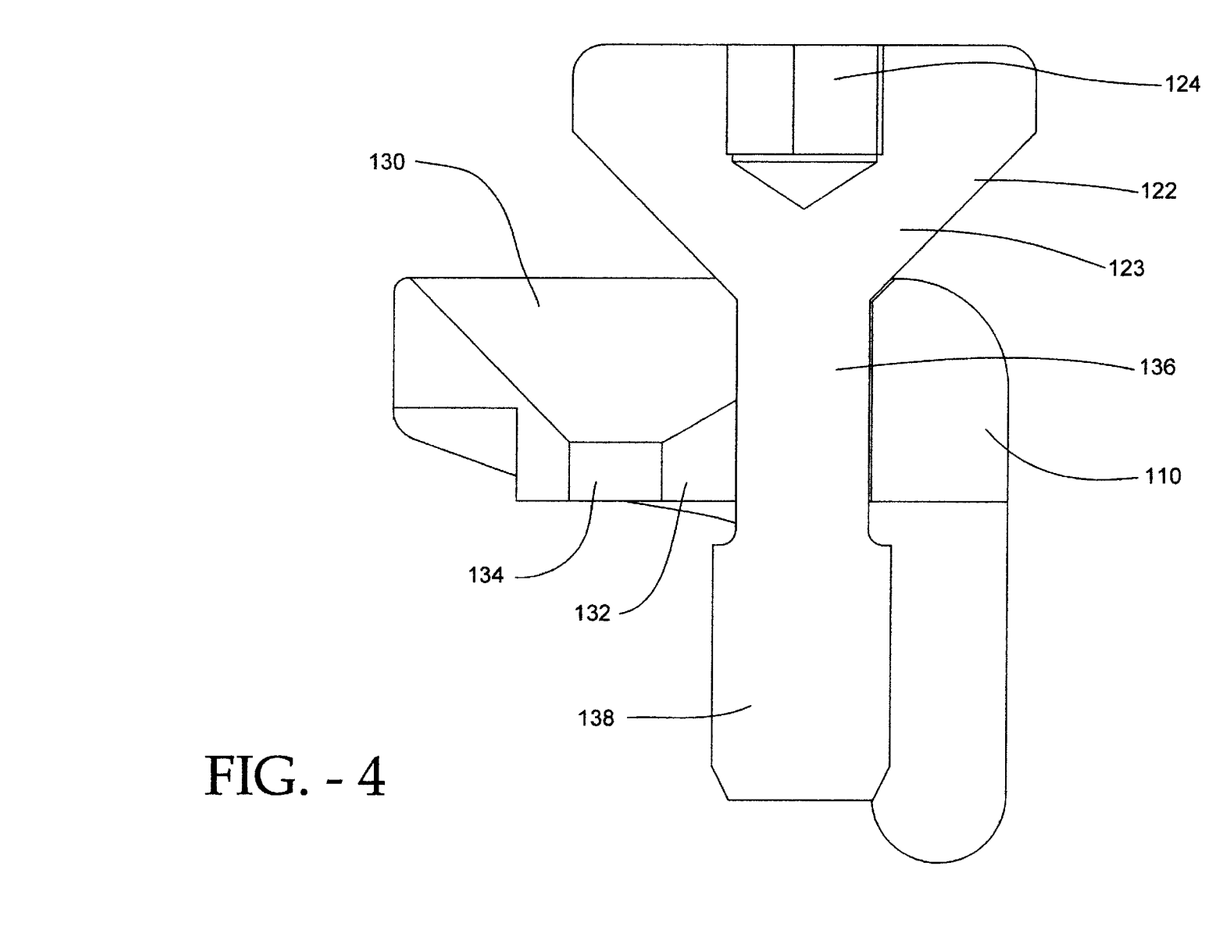
FIG. 4 is cut-away view illustrating the interaction between the fastener and the adjustable wing with the adjustable wing is in a first position.

When the adjustable wing 110 is in the position furthest from the position of the first wing 104, the tapered head 123 of the fastener 122 is substantially out of, and not engaging, the tapered cavity 130 of the adjustable wing 110 (See FIG. 4). As the fastener 122 is rotated, the fastener 122 will continue to engage, and travel further into, the main body 101. As the fastener 122 travels downwardly into the main body 101, the tapered head 123 of the fastener 122 contacts the wall 131 of the tapered cavity 130. The adjustable wing 110 can freely slide back and forth, limited by the end portions 134 of the tapered cavity 130. When the tapered head 123 contacts the wall 131 of the tapered cavity 130, the adjustable wing 110 moves towards the first wing 104 guided by the alignment tab 112 in the alignment track 106. Therefore, the adjustable wing 110 remains substantially parallel to the first wing 104 in this preferred embodiment as the adjustable wing 110 moves toward the first wing 104 (see FIG. 5). It is to be understood that the tab 112 and the track 106 can be eliminated in another embodiment of the invention.

Figure 5:
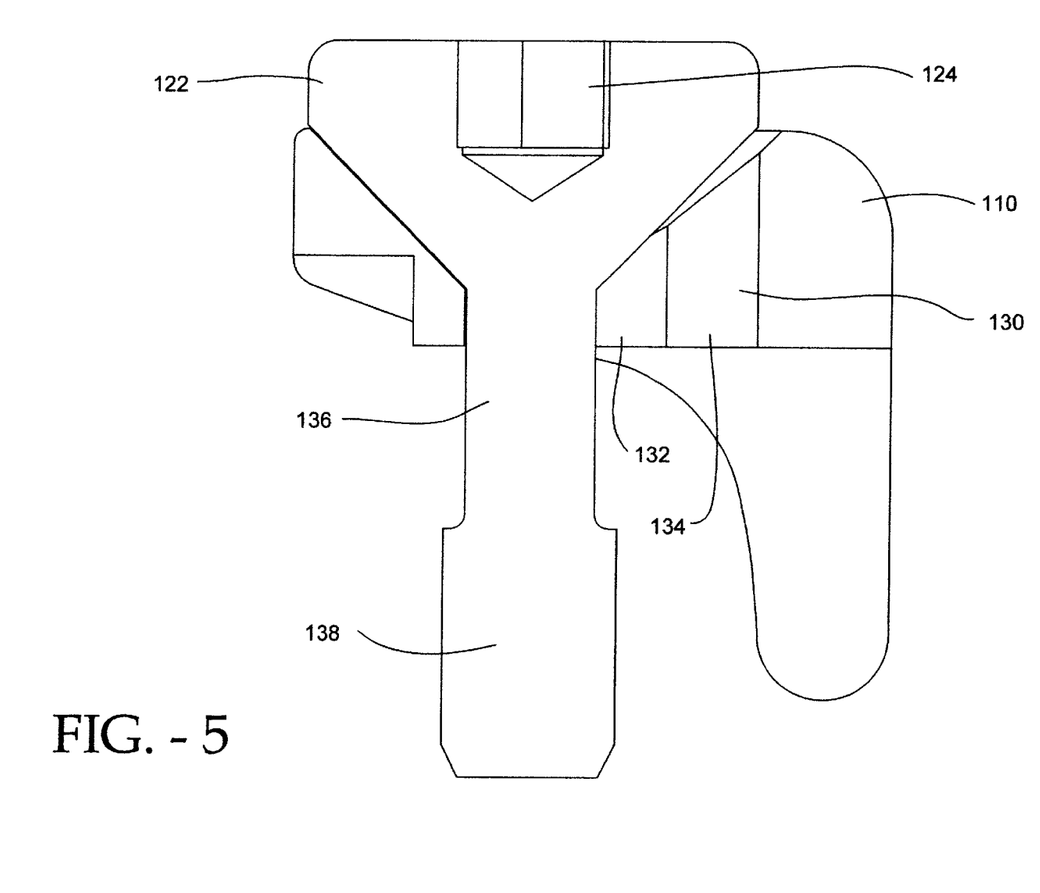
FIG. 5 is a cut-away view illustrating the fastener engaging the adjustable wing with the adjustable wing in a second position.

As shown in FIG. 5, the tapered head of 123 of the fastener 122 is mated in the tapered wall 131 of the adjustable wing 110. Accordingly, with this ramp mechanism, the adjustable wing 110 is urged toward the spinous processes and the first wing 104 and is locked in position at its closest approach to the first wing 104. This arrangement allows the surgeon to loosely assemble the implant in the patient and then urge the adjustable wing closer to the first wing, by rotating fastener 122 into body 110 making the implanting method more tolerant to the anatomy of the patient.

The structure of the spine is of course unique for every patient. Accordingly if the width of the spinous processes is excessive, the adjustable wing can be left in a position that is between that shown in FIG. 4 and that shown in FIG. 5. The separation between the first wing 104 and the adjustable wing 110 can be incrementally adjusted by the number of turns of the fastener 122.

Figure 6:
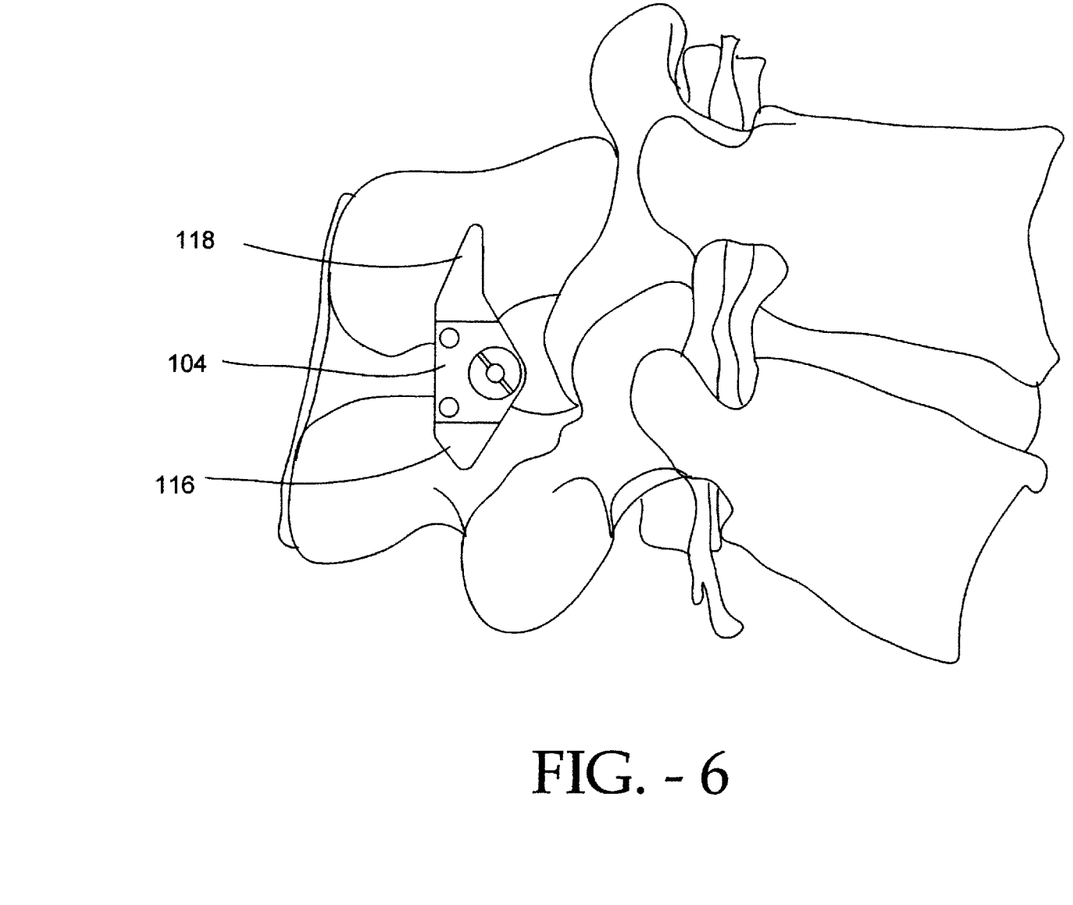
FIG. 6 is a side view illustrating an embodiment of the present invention as implanted between adjacent spinous processes.
Figure 7:
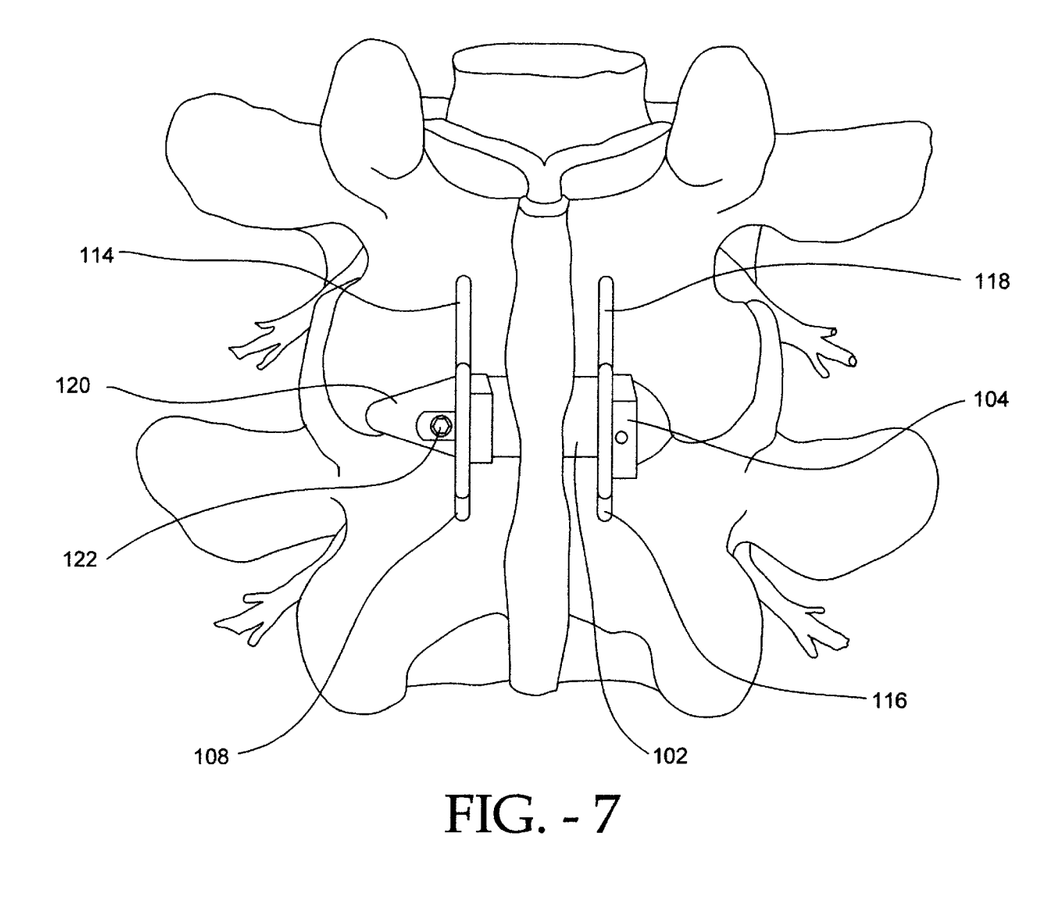
FIG. 7 is a front view of an embodiment of the present invention as implanted between adjacent spinous processes.

FIGS. 6 and 7 illustrate the position of the implant device 100 in a patient. As shown by FIG. 6, the lower portion 116 and upper portion 118 of the first wing 104 function to prevent side-to-side movement, toward and away from the vertebral body ensuring that the implant device 100 remains in place. Similarly, the adjustable wing 110 will also prevent excessive side-to-side movement. The wing also prevents motion in the direction of the main body into the space between the spinous processes.

The foregoing description of preferred embodiments of the present invention has been provided for the purposes of illustration and description. It is not intended to be exhaustive or to limit the invention to the precise forms disclosed. Obviously, many modifications and variations will be apparent to the practitioner skilled in the art. The embodiments were chosen and described in order to best explain the principles of the invention and its practical application, thereby enabling others skilled in the art to understand the invention for various embodiments and with various modifications that are suited to the particular use contemplated. It is intended that the scope of the invention be defined by the following claims and their equivalence.

What is claimed is:

1. An implant for maintaining a space between adjacent spinous processes, the implant comprising:
    a body, having a spacer and an alignment track;
    a wing, having an alignment tab to engage the alignment track on the body; and
    a fastening device that secures the wing to the body;
    whereby when the fastening device engages the body, the wing travels relative to the alignment track.

2. The implant according to claim 1, whereby the body has a tapered front end for urging between adjacent spinous processes.

3. The implant according to claim 1, wherein the body further contains a first wing.

4. The implant according to claim 3, wherein the first wing on the body and the wing provide lateral support to fix the spacer in place between adjacent spinous processes.

5. The implant according to claim 1, wherein the wing further has a cavity extending through.

6. The implant according to claim 5, wherein the cavity is tapered.

7. The implant according to claim 1, wherein the wing travels along the alignment track as a result of the fastening device traveling in a downward vertical position.

8. The implant according to claim 1, whereby the fastening device is a screw with a tapered head.

9. The implant according to claim 8, whereby the tapered head substantially conforms to a cavity in the wing.

10. The implant according to claim 1, wherein the implant does not require any alteration of the spinous process.

11. The implant according to claim 1, wherein the spacer is substantially elliptical in shape.

12. The implant according to claim 1, wherein the spacer is substantially egg-shaped in cross-section.

13. An implant for maintaining a space between adjacent spinous processes, the implant comprising:
    a body, having a spacer adapted to be positioned between adjacent spinous processes, an alignment track, and a first wing element;
    a second wing element, having a cavity extending through, and further having an alignment tab to engage the alignment track;
    a fastening device that can engage the body, such that when the fastening device is tightened, the second wing travels in the alignment track, towards the first wing.

14. The implant according to claim 13, wherein the fastening device is tightened by traveling vertically downward.

15. The implant according to claim 13, wherein the second wing travels horizontally in the alignment track.

16. The implant according to claim 13, wherein the first and second wing element provide lateral support to fix the body in place between adjacent spinous processes.

17. An implant for maintaining a space between adjacent spinous processes, the implant comprising:
    a main body, with a spacer and a tissue expander;
    a wing assembly mateable to the main body, having a wing and a screw; and
    whereby movement of the screw causes movement of the wing along the body.

18. The implant according to claim 17, wherein the spacer is substantially elliptical in shape.

19. The implant according to claim 17, wherein the spacer is substantially egg-shaped in cross-section.

20. The implant according to claim 17, wherein the tissue expander has a tapered front end for urging between adjacent spinous processes.

21. The implant according to claim 17, wherein the wing has a hole extending through.

22. The implant according to claim 21, wherein the hole is tapered.

23. The implant according to claim 17, wherein the body and the wing provide lateral support to fix the spacer in place between adjacent spinous processes.

24. A method for placing an implant between adjacent spinous processes, the method comprising the steps of:
(a) urging a main body between adjacent spinous processes;
(b) positioning a wing relative to the main body; and
(c) tightening a fastener, so that the wing is attached to the main body, and further wherein the tightening of the fastener causes the wing to travel along the main body.

25. The method according to claim 24, wherein the method does not require any alteration of the spinous processes.

26. The method according to claim 24, wherein the travel of the wing in step (c) is towards the body, so that the wing provides additional lateral support.

27. The method according to claim 24, wherein the main body in step (c) contains a tissue expander, a spacer and a body.

28. The method according to claim 24, wherein positioning the wing relative to the main body in step (b) requires an alignment tab of the wing to be placed within an alignment track on the tissue expander.

29. A method for positioning a spacer between adjacent spinous processes, the method comprising the steps of:
(a) urging a spacer between adjacent spinous process;
(b) attaching a wing element to the spacer;
(c) inserting a fastening device into a cavity of the wing element so that the fastening device engages the spacer;
(d) rotating the fastening device, so that the wing element travels relative to the spacer.

30. The method according to claim 29, wherein the method does not require any alteration of the spinous process.

31. An adjustable device for positioning a spacer between adjacent spinous processes, the device comprising:
a main body;
a spacer;
a tissue expander;
a wing, having a hole through;
a wing adjustment device; and
whereby motion by the wing adjustment device causes the wing to move relative to the main body.

32. The device according to claim 31, wherein the spacer is substantially elliptical in shape.

33. The device according to claim 31, wherein the spacer is substantially egg-shaped in cross-section.

34. The device according to claim 31, wherein the tissue expander has a tapered front end for urging between adjacent spinous processes.

35. The device according to claim 31, wherein the wing adjustment device is a screw with a tapered head.

36. The device according to claim 35, wherein the tapered head substantially conforms to the hole in the wing.

37. The device according to claim 31, wherein the main body and wing element provide lateral support to fix the spacer in place between adjacent spinous processes.

38. The device according to claim 31, wherein the device does not require any alteration of the spinous process.

39. An implant for maintaining a space between adjacent spinous processes, the implant comprising:
a body having a spacer and an alignment track;
a wing, having an alignment tab to engage the alignment track on the body;
a fastening device that secures the wing to the body; and
means for adjusting the wing so that the wing can move relative to the body.

40. The implant according to claim 39, whereby the body has a tapered front end for urging between adjacent spinous processes.

41. The implant according to claim 39, wherein the body further contains a first wing.

42. The implant according to claim 39, wherein the wing further has a cavity extending through.

43. The implant according to claim 42, wherein the cavity is tapered.

44. The implant according to claim 39, wherein the implant does not require any alteration of the spinous process.

45. The implant according to claim 39, wherein the spacer is substantially elliptical in shape.

46. The implant according to claim 39, wherein the spacer is substantially egg-shaped in cross-section.

47. An implant for maintaining a spacer between adjacent spinous processes, the implant comprising:
a body, having a spacer adapted to be positioned between adjacent spinous processes, an alignment track, and a first wing element;
a second wing element, having a cavity extending through, and further having an alignment tab to engage the alignment track;
a fastening device that can engage the body; and
means for adjusting the second wing element so that the first wing element and the second wing element provide lateral support to fix the spacer in place between adjacent spinous processes.

48. The implant according to claim 47, wherein the spacer is substantially elliptical in shape.

49. The implant according to claim 47, wherein the spacer is substantially egg-shaped in cross-section.

50. The implant according to claim 47, wherein the implant does not require any alteration of the spinous process.

51. An adjustable device for rigidly fixing a specer between adjacent spinous processes, the device comprising:
a main body with a first wing element;
a spacer;
a tissue expander;
a second wing element, having a hole through;
a wing adjustment device; and
means for adjusting the second wing element so that the first wing element and the second wing element provide lateral support to fix the spacer in place between adjacent spinous processes.

52. The implant according to claim 51, wherein the spacer is substantially elliptical in shape.

53. The implant according to claim 51, wherein the spacer is substantially egg-shaped in cross-section.

54. The implant according to claim 51, wherein the implant does not require any alteration of the spinous process.

55. An implant for maintaining a space between adjacent spinous processes, the implant comprising:
- a body having a spacer;
- a wing;
- a fastening device that secures the wing to the body; and
- whereby when the fastening device engages the body and is rotated, the wing travels relative to the body.

56. An implant for maintaining a space between adjacent spinous processes, the implant comprising:
- a body, having a spacer adapted to be positioned between adjacent spinous processes and a first wing element;
- a second wing element, having a cavity extending through;
- a fastening device that can secure the second wing element to the body, such that when the fastening device is tightened, the second wing element travels towards the first wing.

57. An implant for maintaining a space between adjacent spinous processes, the implant comprising:
- a body having a spacer;
- a wing, having an alignment tab to engage the alignment track on the body;
- a fastening means that secures the wing to the body; and
- whereby adjusting the fastening means causes the wing to move relative to the body.

* * * * *